United States Patent [19]

Rudzena et al.

[11] Patent Number: 4,504,265
[45] Date of Patent: Mar. 12, 1985

[54] CHAMBERS TO ASSURE RELIABLE INFUSION OF MEDICAMENTS AND THE LIKE

[75] Inventors: William L. Rudzena, McHenry; Warren P. Frederick, Wonder Lake; Albert Stone, Buffalo Grove, all of Ill.

[73] Assignee: Baxter Travenol Laboratories, Inc., Deerfield, Ill.

[21] Appl. No.: 404,069

[22] Filed: Aug. 2, 1982

[51] Int. Cl.³ .............................................. A61M 5/14
[52] U.S. Cl. ........................................ 604/86; 604/246
[58] Field of Search ................. 604/56, 82, 83, 85–90, 604/93, 121, 131, 149, 151, 152, 245–247, 249, 256, 414, 191

[56] References Cited

U.S. PATENT DOCUMENTS

| 3,177,870 | 4/1965 | Salem, Jr. et al. | |
|---|---|---|---|
| 3,330,282 | 7/1967 | Visser et al. | 604/90 |
| 3,345,986 | 10/1967 | Roberts et al. | 604/249 |
| 3,788,524 | 1/1974 | Davis et al. | 604/414 |
| 3,844,283 | 10/1974 | Dabney | 604/246 |
| 3,905,905 | 9/1975 | O'Leary et al. | |
| 3,951,145 | 4/1976 | Smith | |
| 3,965,897 | 6/1976 | Lundquist | 604/246 |
| 3,967,620 | 7/1976 | Noiles | |
| 3,976,068 | 8/1976 | Lundquist | 604/83 |
| 4,005,710 | 2/1977 | Zeddies et al. | |
| 4,009,715 | 3/1977 | Forberg et al. | |
| 4,066,556 | 1/1978 | Vaillancourt | |
| 4,219,022 | 8/1980 | Genese | |
| 4,223,695 | 9/1980 | Muetterties | |
| 4,237,880 | 12/1980 | Genese | |
| 4,276,170 | 6/1981 | Vaillancourt | |

FOREIGN PATENT DOCUMENTS

0705392 3/1954 United Kingdom .

OTHER PUBLICATIONS

"Therapeutic Problems Arising From the Use of the Intravenous Route for Drug Administration", Gould et al., *The Journal of Pediatrics*, vol. 95, No. 3, pp. 465–471, (1979).

"New Retrograde Method for Administering Drugs Intravenously", Benzing, III et al., *Pediatrics*, vol. 52, No. 3, pp. 420–425, (9/73).

"Methods for Intravenous Drug Administration in the Pediatric Patient", Leff et al., *The Journal of Pediatrics*, vol. 98, No. 4, pp. 631–635, (1981).

*Primary Examiner*—C. Fred Rosenbaum
*Assistant Examiner*—Michelle N. Lester
*Attorney, Agent, or Firm*—John P. Kirby, Jr.; Bradford R. L. Price; Garrettson Ellis

[57] ABSTRACT

In a fluid administration set of otherwise conventional design, an in-line chamber is provided having an inlet and outlet port communicating with the chamber and defining part of the path of flow through the set. A sealing piston is slidably movable by fluid pressure within the chamber and capable of occupying first positions in which the sealing piston isolates fluid in the chamber adjacent the inlet port from fluid in the chamber adjacent the outlet port. The sealing piston also can occupy at least one second position in which unlimited fluid flow is permitted between the inlet port and outlet port. A third port is provided for intermittently inserting a critical fluid into the chamber on the side of the sealing piston facing the outlet port. Thus the piston can be driven into the first position from the second position by this insertion, to prevent mixing of the critical fluid with fluid on the side of the piston facing the inlet port until the critical fluid has substantially passed through the outlet port and the piston moves to the second position. This permits the reliable, prompt administration of essentially the entire dose of a critical medication, particularly at low flow rates.

14 Claims, 3 Drawing Figures

CHAMBERS TO ASSURE RELIABLE INFUSION OF MEDICAMENTS AND THE LIKE

TECHNICAL FIELD AND PRIOR ART

Sets for the administration of solutions and blood to patients by the parenteral route are well known and commercially available in a wide variety of types. Most of them carry injection sites for the substantially aseptic addition of supplemental medications to the patient. Various types of these injection sites include a Y-site, carrying a resealable latex diaphragm for needle puncture, and an enlarged latex bulb for receiving needle punctures in resealable manner. Other types of injection sites are also used.

However, a problem has been identified which particularly arises when slow intravenous flow rates are used. It is often desired to promptly administer a drug, although it is necessary for the overall rate of intravenous flow into the patient to be quite low, for example 1 to 10 ml. per hour. This need particularly arises in the pediatric field. The problem is that at such flow rates, many drugs, added to a conventional injection site of a set, can take a surprisingly long time for most of the dose of drug to find its way into the patient. Thus the drug can be delivered through the set, but it still may take hours at a low flow rate for the drug to be substantially administered to the patient in the complete, desired dose, apparently in part because of specific gravity differences from the main parenteral solution.

This surprising problem has been discussed in the article of Teddie Gould et al. entitled "Therapeutic Problems Arising from the Use of the Intravenous Route for Drug Administration", *The Journal of Pediatrics*, Volume 95, pp. 465-471 (1979). As described therein, the problem can become very significant when working with neonatal patients, with surprising delays in the administration of certain antibiotics and other medications. At one point the article states that the injection of Gentamicin into a Y-site of a set, where the set flow rate was 3 ml. per hour, "... resulted in 30% of the drug remaining at the Y site at the end of 8 hours"!

In accordance with this invention, an element for a fluid administration set, which set otherwise may be of conventional design, is provided to greatly reduce or eliminate the problem outlined above by initially isolating the bolus of critical solution desired to be added to the flow line of the set from fluids upstream of the critical solution. Thus, as the flow continues through the set, even at a low rate, the bolus of critical solution is necessarily forced on downstream to the patient or other delivery site. Thereafter, in an automatic manner, upstream fluids can once again flow through the set.

Another advantage of the invention of this application is that it permits a set to be connected to a positive flow pump, which prevents back flow through the set. Nevertheless, the critical fluid may be inserted into the set, despite the connection with the pump, and without forcing a sudden bolus of fluid downstream to the patient, which may be undesirable. At the same time, the critical fluid is isolated from upstream fluids after insertion into the set, and thereafter it flows in accordance with the normal flow rate of the set, while remaining isolated until it has passed on its way downstream from the in-line chamber.

While the fluid administration set of this invention is typically used in the medical field for the administration of parenteral solutions, it is contemplated that it may find use in other fields as well, wherever the problem specified above interferes with optimum fluid delivery operations.

DESCRIPTION OF THE INVENTION

In accordance with this invention, a fluid administration set is provided with an in-line chamber having an inlet port and an outlet port communicating with the chamber and defining part of the path of flow through the set. A sealing piston, slidingly movable by fluid pressure within the chamber, is provided, being capable of occupying first positions in which the sealing piston isolates fluid in the chamber adjacent the inlet port from fluid in the chamber adjacent the outlet port.

The sealing piston can also be moved to occupy at least one second position, typically adjacent the outlet port. Means are provided permitting unlimited fluid flow between the inlet port and the outlet port in the second position, bypassing the piston.

Third port means are also provided for intermittent inserting a critical fluid such as an antibiotic or other medication into the chamber on the side of the sealing piston facing (communicating with) the outlet port.

Fourth port means may be provided for removing fluid from the chamber on the side of the sealing piston facing (communicating with) the inlet port, to permit the piston to be moved toward the inlet port by fluid pressure as the critical fluid is inserted into the chamber on the side of the sealing portion facing the outlet port.

Accordingly, even if the administration set is connected with a pump which positively controls flow through the set, it is possible to insert the critical fluid into the downstream side of the chamber, causing the piston to move toward the inlet port by fluid pressure as the critical fluid is inserted, with the contents of the chamber on the side of the sealing piston facing the inlet port moving out of the fourth port. This is thus permitted to happen even when the positive flow pump is controlling flow through the set at a position upstream from the inlet port, preventing back flow through the inlet port.

As the result of this, the set may initially operate with the piston in its second position, which permits flow through the set. One may then insert an injection needle, for example, into the third port means and insert a bolus of critical fluid into the chamber on the side of the sealing piston facing the outlet port. The pressure of this fluid causes the piston to move from its second position to a first position. Thus the contents of the bolus of material added are isolated by the piston from the remaining contents of the chamber.

A second injection syringe, for example, may be inserted into the fourth port means to receive excess solution from the chamber which is displaced by the critical fluid coming in and causing the piston to displace from the second position to a first position. Thereafter, as flow continues through the set, the piston is moved back towards its second position by fluid pressure of normal flow through the set, but until it reaches the second position there is no intermixing of the upstream contents of the in-line chamber and the bolus of critical material.

When the piston is once again pressed by normal flow of fluid through the set into its second position, the solution upstream of the piston can once again flow through the set permitting intermingling with the bolus of critical fluid, but by that time most of the critical fluid has been sent on its way toward the patient, and thus the intermixing is low, if any. The result of this is that substantially all of the critical fluid is applied to the patient in a minimum time, consistent with the flow rate provided.

Typically the second position of the sealing piston is its closest sliding position to the outlet port, with the piston being slidable in a cylindrical portion of the chamber and the outlet port being positioned at or adjacent one end thereof.

The preferred means for permitting unlimited fluid flow between the inlet port and outlet port in the second position, while isolating fluid in the chamber adjacent the inlet port from the fluid in the chamber adjacent the outlet port in the first positions, may be provided by an axial groove positioned on the inner wall of the chamber and of a length to permit shunting of fluid flow around the sealing piston when the piston is in the second position, but not when the piston is in a first position. It is also desirable for the groove to be narrow enough so that the sealing piston can be moved by pressurized fluid entering the third port from the second to a first position. Typically the groove may be 0.03 inch wide, 0.015 inch deep, and 0.2 inch long. With these small dimensions, a syringe can penetrate a resilient, needle-pierceable, resealable diaphragm covering the third port, and a bolus of medicament can be added with a normal squeeze of the syringe plunger. This same normal squeeze of the syringe plunger is sufficient to provide enough pressure, despite the presence of the small groove, to displace the sealing piston away from the groove into one of its first positions, since the axial groove is thin enough so that the pressure causing the piston to move is not dissipated before the piston does move to a first position. Thereafter the piston moves in a quantitative manner with respect to fluid flow in either direction since it seals and isolates the fluids on either side of it.

It is generally desirable to minimize the fluid volume of the set downstream of the sealing piston and chamber, to prevent pooling of the bolus of critical fluid added as well as minimizing the time of delivery of the bolus of critical fluid, particularly at very low flow rates.

DESCRIPTION OF THE SPECIFIC EMBODIMENT

Figure 1:
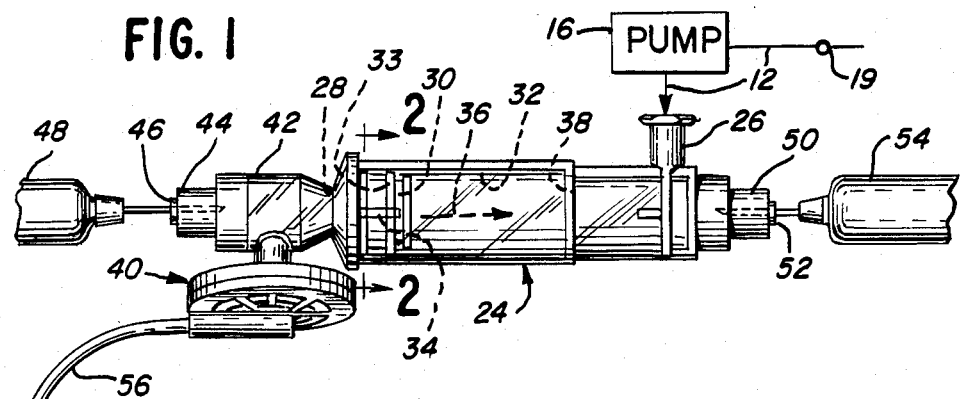
FIG. 1 is a plan, partially schematic view of an IV administration set utilizing the in-line chamber of this invention, with portions of the set being shown schematically.
Figure 2:
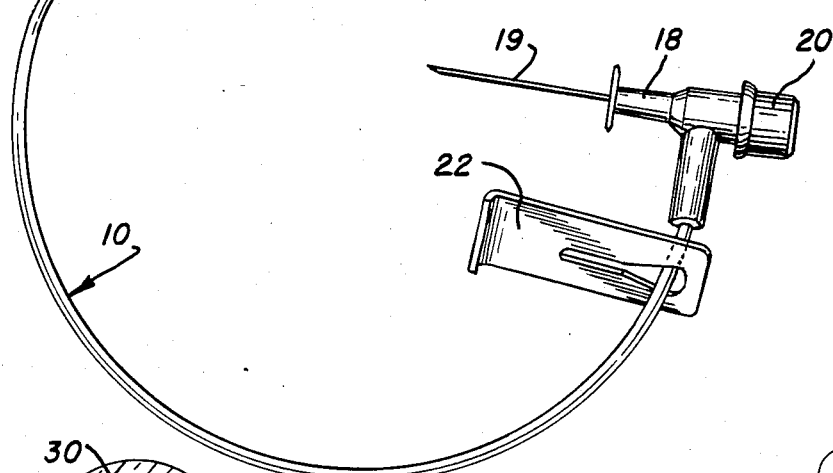
FIG. 2 is a sectional view taken along line 2—2 of FIG. 1.
Figure 2:
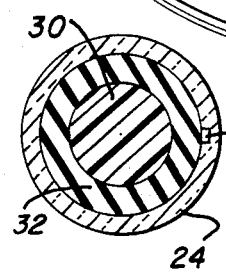

Referring to FIGS. 1 and 2, a solution administration set 10 is disclosed, which may be of generally conventional design except as otherwise indicated herein. The upstream attachment portion 12 to set 10 is shown in a schematic manner, terminating in a spike connector 14 or the like as may be desired, and optionally containing conventional injection sites, a drip chamber, and a tube segment for interaction with a positive flow control pump 16 as desired, for the administration of measured amounts of solution through the set. At its other end, set 10 may carry an IV needle hub 18, shown to be carrying IV needle 19, latex injection site 20, and slide clamp 22, all of which may be of conventional design.

In accordance with this invention, there is provided to set 10 an in-line chamber 24, defining inlet port 26 and outlet port 28 communicating with chamber 24, and defining part of the path of flow through set 10.

Sealing piston 30, which may be made of rubber or the like, is slidingly movable by fluid pressure within cylindrical bore portion 32 of chamber 24. As shown in FIG. 1, piston 30 is occupying its second position in which the sealing rings 33 of piston 30 are bypassed by axial groove 34, positioned on the inner wall of chamber 24 as shown, so that flow from inlet port 26 may pass chamber 24 and through outlet port 28 via axial groove 34 when piston 30 is in its second position.

Piston 30 may be moved to the right as indicated by arrow 36 into any of a series of first positions, with the rightward motion of piston 30 being limited by annular ledge 38 of chamber 24. As soon as one of sealing rings 33 of piston 30 is no longer traversed by groove 34, the portion of the chamber 24 to the right of piston 34 which faces inlet port 26 becomes isolated from the portion of the chamber 24 between piston 34 and outlet port 28.

Downstream from outlet port 28 a conventional 0.22 micron bacterial filter 40 positioned flat in a housing and of typically conventional design, may be provided.

An auxiliary chamber 42 is also provided downstream from outlet port 28, which carries third port 44 which, in turn, is closed with a resilient, needle-pierceable, resealable diaphragm 46 made typically of natural rubber latex. As shown, a syringe needle 48 is in the process of penetrating latex diaphragm 46 for communication into third port 44 for the application of a bolus of critical medication such as an antibiotic to the set.

There is also provided a fourth port 50 which is closed with a similar diaphragm 52 of resealable, needle-pierceable natural rubber latex or the like, and a second syringe needle 54 is shown penetrating diaphragm 52.

Accordingly, when it is desirable to insert a bolus of critical medication one may insert the two syringe needles 48, 54 as shown into third port 44 and fourth port 50. The slide clamp 22 is engaged to close the set 10 from the needle 19. One then firmly squeezes syringe needle 48, causing the bolus of antibiotic or other material to flow into auxiliary chamber 42. The pressure provided by this flow causes piston 30 to move to the right in the direction of arrow 36 from its second position into a first position by a distance dependent upon the total amount of the bolus administered from syringe 48. As piston 30 moves to the right, in the event that flow upstream through the upper portion 12 of set 10 is blocked by its engagement with pump 16, parenteral solution can pass out of fourth port 50 into syringe 54, to make room for the sliding motion of piston 30 to the right. After the bolus is injected from the syringe needle 48, the slide clamp 22 is disengaged.

When piston has disengaged from slot 34, there is no communication between the areas of chamber 24 which are to the right and left of piston 30, respectively facing inlet port 26 and outlet port 28. Thus the contents of the bolus of material provided through syringe 48 cannot intermingle with upstream fluids. Instead, as upstream pressure causes parenteral solution to pass downwardly through set 10, piston 30 slowly moves back to the left toward its second position as shown. At the same time, the bolus of critical material passes downwardly through filter 40 and into tubing 56, on its way to needle 19 and the patient. By the time that piston 30 has once again reached its second position, again opening flow through slot 34 so that solution may pass from the chamber area upstream of piston 30 to the chamber area downstream of piston 30 and outlet port 28, most of the bolus of critical material will have already passed into tube 56 on its way to the patient. Thus the structure of this invention assures the prompt, largely unmixed administration of a bolus of critical material from syringe 48 when applied through third port 44 into the system of this invention.

After application of the bolus of material, causing piston 30 to move to the right into a first position, both syringes 48 and 54 may be withdrawn, and the set will operate in the manner specified above.

It can also be seen that repeated boluses of critical medication or the like can be added at any time to the system of this invention without disconnecting it from the pump 16, or without flooding any drip chambers upstream in the set, which is another disadvantage that can occur, apart from this invention, even when an upstream portion 12 of the set is not connected to a pump, upon addition of a downstream bolus of material.

Figure 3:
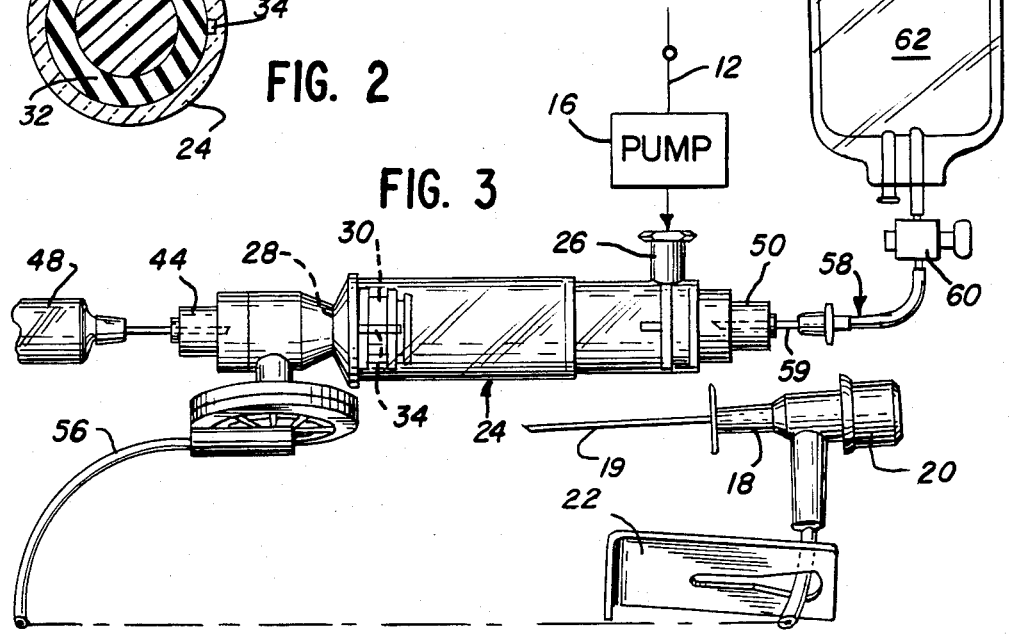
FIG. 3 is a plan view, with some portions shown schematically, of a modification of the structure as shown in FIG. 1.

Turning to FIG. 3, an identical set portion is provided, having identical reference numerals to that of FIG. 1, with the exception that instead of a syringe needle analogous to syringe needle 54, a needle system 58 is provided. Needle 59 is connected through stopcock 60 to a small, collapsible plastic bag 62 which may be used to receive excess solution corresponding in volume to the volume of the bolus provided through syringe needle 48.

As the result of this invention, there can be reliably administered to pediatric patients and others as may be desired a substantially complete bolus of critical medication, with the confidence that substantially all of the bolus will pass immediately downstream to the patient, even though only low flows of fluid volume, for example 1 to 10 cc. per hour, are passing through the set. This invention provides the combination of low flow solution administration, and typically pumped solution administration, coupled with the possibility for convenient, rapid, and reliable applications of substantially an entire bolus of critical medication which can be expected to pass to the patient almost as quickly as would be ideally expected by the flow rate utilized.

The above has been offered for illustrative purposes and is not intended to limit the scope of the invention of this application, which is as defined in the claims below.

That which is claimed is:

1. In a fluid administration set, an in-line chamber, an inlet port and an outlet port communicating with said chamber and defining part of the path of flow through said set, a sealing piston slidingly movable by fluid pressure within said chamber and capable of occupying first positions in which said sealing piston isolates fluid in said chamber adjacent the inlet port from the fluid in the chamber adjacent the outlet port, said sealing piston also being capable of occupying at least one second position, means permitting unlimited fluid flow between said inlet port and outlet port in the second position, and third port means for intermittently inserting a critical fluid into said chamber on the side of said sealing piston facing the outlet port, and fourth port means provided for removing fluid from the chamber on the side of said sealing piston facing the inlet port, to permit said piston to be moved toward the inlet port by fluid pressure as said critical fluid is inserted into the chamber on the side of said sealing piston facing the outlet port, whereby said piston in a first position prevents mixing of said critical fluid with fluid on the side of the piston facing the inlet port until said piston moves to the second position.

2. The set of claim 1 in which said third and fourth port means are each sealed with a resilient, needle-pierceable, resealable diaphragm.

3. In a fluid administration set, an in-line chamber, an inlet port and an outlet port communicating with said chamber and defining part of the path of flow through said set, at least part of said chamber being of cylindrical shape, a sealing piston sealingly movable by fluid pressure within said cylindrical part of the chamber and capable of occupying first positions in which said sealing piston isolates fluid in said chamber adjacent the inlet port from fluid in the chamber adjacent the outlet port, said sealing piston also being capable of being moved by fluid pressure to at least one second position adjacent the outlet port, means permitting unlimited fluid flow between said inlet port and outlet port in the second position, third port means for intermittently inserting a critical fluid into said chamber on the side of said sealing piston facing the outlet port, and fourth port means provided for removing fluid from the chamber on the side of said sealing piston facing the inlet port, to permit said piston to be moved toward the inlet port by fluid pressure as said critical fluid is inserted into the chamber on the side of said sealing piston facing the outlet port, whereby said piston, after being moved to a first position by insertion of said critical fluid, prevents mixing of said critical fluid with fluid on the side of the piston facing the inlet port, and thereafter fluid pressure in the set from the inlet toward the outlet can drive the piston back toward the second position so that, when the critical fluid has substantially passed through the outlet port, said piston moves into the second position, permitting unlimited additional flow through said set.

4. The set of claim 3 in which a portion thereof upstream from said inlet port is in engagement with a flow metering pump to positively control flow therethrough.

5. The set of claim 3 in which said means for permitting unlimited fluid flow between the inlet port and the outlet port in the second position comprises an axial groove positioned and of a length to permit shunting fluid flow around said sealing piston when said piston is in the second position, but not when said piston is in a first position.

6. The set of claim 5 in which said third and fourth port means are each sealed with a resilient, needle-pierceable, resealable diaphragm.

7. In a fluid administration set, an in-line chamber, an inlet port and an outlet port communicating with said chamber and defining part of the path of flow through said set, filter means downstream from said outlet port, at least part of said chamber being of cylindrical shape, a sealing piston sealingly movable by fluid pressure within said cylindrical part of the chamber and capable of occupying first positions in which said sealing piston isolates fluid in said chamber adjacent the inlet port from fluid in the chamber adjacent the outlet port, said sealing piston also being capable of being moved by fluid pressure to at least one second position adjacent the outlet port, means permitting unlimited fluid flow between said inlet port and outlet port in the second position, third port means for intermittently inserting a critical fluid into said chamber on the side of said sealing piston facing the outlet port, and fourth port means provided for removing fluid from the chamber on the side of said sealing piston facing the inlet port, to permit said piston to be moved toward the inlet port by fluid pressure as said critical fluid is inserted into the chamber on the side of said sealing piston facing the outlet port, whereby said piston, after being moved to a first position by insertion of said critical fluid, prevents mixing of said critical fluid with fluid on the side of the piston facing the inlet port, and thereafter fluid pressure in the set from the inlet toward the outlet can drive the piston back toward the second position so that, when the critical fluid has substantially passed through the outlet port, said piston moves into the second position, permitting unlimited additional flow through said set.

8. The set of claim 3 in which the second position of the sealing piston is its closest sliding position to the outlet port.

9. The set of claim 1 in which said second position of the sealing piston is its closest sliding position to the outlet port.

10. The set of claim 9 in which the inner wall of said chamber defines an axial groove positioned and of a length to permit shunting fluid flow around said sealing piston when said piston is in the second position but not when said piston is in a first position, said groove being narrow enough so that said sealing piston can be moved by pressurized fluid entering the third port from the second to a first position.

11. The set of claim 1 in which a portion thereof upstream from said inlet port is in engagement with a flow metering pump to positively control flow therethrough.

12. The set of claim 1, further comprising a bag in selective communication with said fourth port means and said chamber.

13. The set of claim 12, further comprising a stopcock intermediate said fourth port means and said bag for providing the selective communication between said bag and both of said fourth port means and said chamber.

14. The set of claim 1, further comprising a syringe needle in selective communication with both of said fourth port means and said chamber.

* * * * *